(12) United States Patent
Sandrin et al.

(10) Patent No.: US 11,529,121 B2
(45) Date of Patent: Dec. 20, 2022

(54) MULTIPULSE ELASTOGRAPHY METHOD

(71) Applicant: ECHOSENS, Paris (FR)

(72) Inventors: Laurent Sandrin, L'Hay les Roses (FR); Cécile Bastard, Paris (FR)

(73) Assignee: ECHOSENS, Paris (FR)

( * ) Notice: Subject to any disclaimer, the term of this patent is extended or adjusted under 35 U.S.C. 154(b) by 121 days.

(21) Appl. No.: 14/768,541

(22) PCT Filed: Feb. 19, 2014

(86) PCT No.: PCT/EP2014/053264
§ 371 (c)(1),
(2) Date: Aug. 18, 2015

(87) PCT Pub. No.: WO2014/128182
PCT Pub. Date: Aug. 28, 2014

(65) Prior Publication Data
US 2015/0374338 A1    Dec. 31, 2015

(30) Foreign Application Priority Data
Feb. 19, 2013  (FR) ........................................ 1351405

(51) Int. Cl.
*A61B 8/00* (2006.01)
*A61B 8/08* (2006.01)
*G01S 7/52* (2006.01)

(52) U.S. Cl.
CPC ............ *A61B 8/485* (2013.01); *A61B 8/5207* (2013.01); *A61B 8/5223* (2013.01); *G01S 7/52042* (2013.01); *G01S 7/52046* (2013.01)

(58) Field of Classification Search
CPC ..... A61B 8/485; A61B 8/5207; A61B 8/5223; G01S 7/52042; G01S 7/52046
See application file for complete search history.

(56) References Cited

U.S. PATENT DOCUMENTS

2005/0065426 A1*  3/2005  Porat ................... A61B 5/0051
                                                       600/407
2010/0069751 A1    3/2010  Hazard et al.
(Continued)

FOREIGN PATENT DOCUMENTS

CN       102151152 A      8/2011
EP       2 294 983 A1     3/2011
(Continued)

OTHER PUBLICATIONS

International Search Report as issued in International Patent Application No. PCT/EP2014/053264, dated May 12, 2014.
(Continued)

*Primary Examiner* — Rajeev P Siripurapu
(74) *Attorney, Agent, or Firm* — Pillsbury Winthrop Shaw Pittman LLP

(57) ABSTRACT

A multipulse elastography method for the quantitative measurement of at least one mechanical property of a viscoelastic medium having an ultrasonic signal after ultrasonic illumination, the method including defining characteristics of at least two mechanical pulses; generating the at least two mechanical pulses for which characteristics are defined in a viscoelastic medium; monitoring a propagation of at least two shear waves generated by the at least two mechanical pulses using acquisition and emission of ultrasonic signals, in the viscoelastic medium, and calculating at least one mechanical property of said viscoelastic medium using said acquisitions of said ultrasonic signals.

15 Claims, 3 Drawing Sheets

(56) References Cited

U.S. PATENT DOCUMENTS

2010/0256530 A1    10/2010  Varghese et al.
2011/0301468 A1*   12/2011  Sandrin ............... A61B 5/6843
                                                            600/459
2012/0158323 A1     6/2012  Hazard et al.

FOREIGN PATENT DOCUMENTS

| FR | 2 843 290 A1 | 2/2004 |
| KR | 10-2011-0090202 A | 8/2011 |
| WO | WO 2011/007278 A2 | 1/2011 |
| WO | WO 2011/064688 A1 | 6/2011 |
| WO | WO 2011/132014 A1 | 10/2011 |

OTHER PUBLICATIONS

Office Action as issued in Indian Patent Application No. 4890/CHENP/2015, dated Jan. 10, 2020.
Office Action as issued in Korean Patent Application No. 10-2015-7024857, dated Jun. 24, 2020.

* cited by examiner

MULTIPULSE ELASTOGRAPHY METHOD

CROSS REFERENCE TO RELATED APPLICATIONS

This application is the U.S. National Stage of PCT/EP2014/053264, filed Feb. 19, 2014, which in turn claims priority to French Patent Application No. 1351405, filed Feb. 19, 2013. The contents of all of these applications are incorporated herein by reference in their entirety.

TECHNICAL FIELD OF THE INVENTION

This invention relates to a multipulse elastography method for the quantitative measurement of at least one mechanical property of a viscoelastic medium having an ultrasonic signal after ultrasonic illumination. In one non-limitative application, the invention relates to a multipulse elastography method for the quantitative measurement of the elasticity and viscosity of a human or animal organ, for example hepatic tissue.

STATE OF PRIOR ART

A method is known for simultaneously observing propagation of a low frequency pulse shear wave to a large number of points in a diffusing viscoelastic medium. This is done by emitting ultrasonic compression waves at ultrahigh speed to obtain a sequence of measurements in the medium, and the measurements thus obtained are then processed off-line or possibly in real time to determine movements of the medium during propagation of the shear wave.

Patent application FR2843290 describes a device for measuring the elasticity of an organ having an ultrasonic signal after ultrasonic illumination, the device comprising an ultrasonic transducer and a slaved electrodynamic actuator designed to vibrate the transducer at low frequency to emit a shear wave in the tissue. The share wave has a frequency band in which the central frequency is known, the frequencies surrounding the central frequency are highly attenuated such that data can only be obtained on frequencies very close to the central frequency. Consequently, the measurements made cannot fully characterise the tissue.

A technology called ARFI (Acoustic Radiation Force Impulse) elastography is also known in which tissues are moved by the action of a force produced by the radiation pressure generated by an ultrasonic beam. This displacement corresponds to the generation of shear stresses in the tissues and results in the propagation of a shear wave. In the case of ARFI, the shear wave is very quickly attenuated and generally propagates over less than one wavelength. It is difficult to study the frequency characteristics of the shear wave under these conditions. Therefore scientists who use this technique usually study the rise time or the relaxation time and displacement amplitudes (see patent US 2010/069751 and WO 2011/064688). Displacements induced in tissues can be modulated by modulating the ultrasonic beam, in other words the ultrasonic emissions, for example by modulating its frequency, amplitude or rate. Therefore some teams in turn have proposed to use several types of ultrasonic excitation with different properties in order to modulate the response of the tissue in terms of maximum observed displacement, rise time or relaxation time (US patent 2010/069751). However, tissue displacements and particularly their frequency content cannot be precisely modulated by modulating ultrasonic emission parameters. Displacements generated by the force due to the radiation pressure depend on the tissue absorption factor.

This is the context in which the invention discloses an elastography method capable of overcoming the disadvantages of prior art and particularly an elastography method for quickly obtaining precise quantitative measurements of the mechanical properties of a human or animal organ.

PRESENTATION OF THE INVENTION

The invention discloses a multipulse elastography method for the quantitative measurement of at least one mechanical property of a viscoelastic medium having an ultrasonic signal after ultrasonic illumination, said method including the following steps:
  define the characteristics of at least two mechanical pulses,
  use an electrodynamic actuator to generate said at least two mechanical pulses,
  monitor the propagation of at least two shear waves generated by said at least two mechanical pulses using ultrasonic signal emission and acquisition means, in a viscoelastic medium,
  calculate at least one mechanical property of said viscoelastic medium using said acquisitions of said ultrasonic signals.

In one non-limitative embodiment, at least one of the defined characteristics is different for each mechanical pulse. A characteristic of the mechanical pulse non-limitatively refers to a central frequency, an amplitude, a number of periods and/or a determined time profile.

The disclosed invention can be used to make a pulsed elastography acquisition composed of a series of pulses, for example with different characteristics such as different determined central frequencies. In this non-limitative example, each pulse can be used to study a frequency band around its determined central frequency. This special feature can characterise the medium over a wide frequency range.

Apart from the characteristics mentioned in the previous section, the method according to the invention may have one or several complementary characteristics among the following, taken individually or in any technically feasible combination.

In one non-limitative embodiment of the multipulse elastography method, the method comprises a step in which the generation step, the monitoring step and the calculation step are reiterated.

In one non-limitative embodiment of the multipulse elastography method, the reiteration is made between 1 and 1000 times, and preferably between 1 and 20 times.

In one non-limitative embodiment of the multipulse elastography method, the at least one different characteristic is the amplitude.

In one non-limitative embodiment of the multipulse elastography method, the amplitude of each mechanical pulse is between 10 µm and 10 mm, and is preferably between 100 µm and 5 mm.

In one non-limitative embodiment of the multipulse elastography method, the at least one different characteristic is the time profile and/or the number of periods.

In one non-limitative embodiment of the multipulse elastography method, the at least one different characteristic is the central frequency.

In one non-limitative embodiment of the multipulse elastography method, the central frequency of each mechanical pulse succeeding a mechanical pulse is less than the central frequency of the preceding mechanical pulse.

In one non-limitative embodiment of the multipulse elastography method, the central frequency of each mechanical pulse succeeding a mechanical pulse is more than the central frequency of the preceding mechanical pulse.

In one non-limitative embodiment of the multipulse elastography method, the frequency bands of at least two mechanical pulses partially overlap.

In one non-limitative embodiment of the multipulse elastography method, the central frequency of each mechanical pulse is between 10 Hz and 5000 Hz, and is preferably between 20 Hz and 1000 Hz.

The invention also relates to a multipulse elastography device comprising a vibration generator capable of generating a plurality of mechanical pulses, each mechanical pulse generating a shear wave in a viscoelastic medium, and at least one ultrasonic transducer capable of emitting and acquiring ultrasonic signals, said device being characterised in that it is capable of implementing the steps in the multipulse elastography method according to the invention.

In one non-limitative embodiment, the vibration generator is a slaved electrodynamic actuator and is capable of making the transducer vibrate at low frequency (this vibration is a mechanical pulse) to emit a shear wave in the tissue. Therefore this invention discloses how the control characteristics (and therefore the mechanical pulse) of this electrodynamic actuator can be modified to precisely modulate the characteristics of the generated shear wave and particularly its frequency content. The characteristics of a shear wave generated by a mechanical pulse with known characteristics can be calculated, for example using Green elastodynamic functions.

BRIEF DESCRIPTION OF THE FIGURES

Other characteristics and advantages of the invention will become clear from the following purely illustrative and non-limitative description that should be read with reference to the appended drawings in which.

Elements common to the figures have the same reference numbers in all the figures.

DETAILED DESCRIPTION OF AT LEAST ONE NON-LIMITATIVE EMBODIMENT OF THE INVENTION

Figure 1:
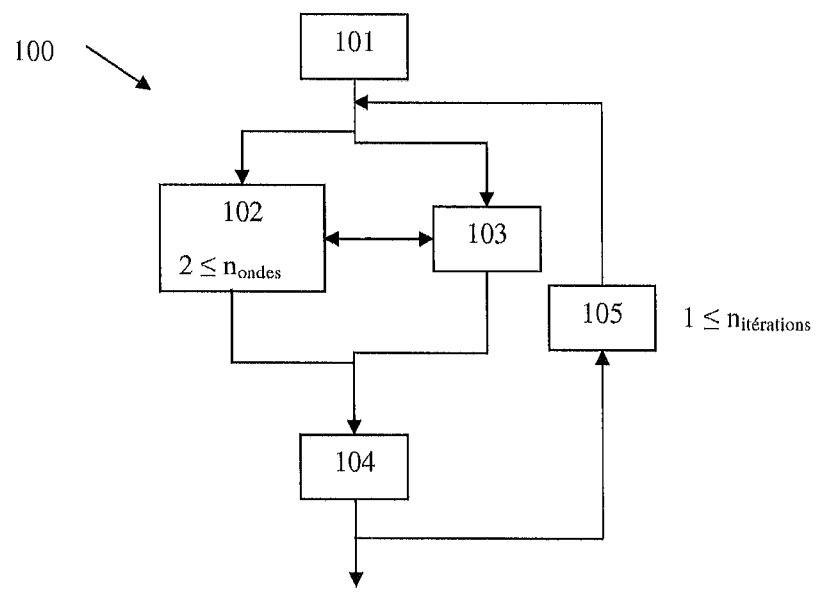
FIG. 1 is a block diagram of the steps in a multipulse elastography method according to the invention.

FIG. 1 illustrates a block diagram of the steps in a multipulse elastography method 100 according to the invention.

The multipulse elastography method 100 comprises in particular a step 101 to define the characteristics of at least two low frequency mechanical pulses. In this example, at least one of the defined characteristics is different for each pulse.

Non-limitatively, a mechanical pulse may be characterised by a central frequency, an amplitude, a number of periods and/or a determined time profile.

Thus during this definition step 101, an operator can for example define a ramp type time profile for a first pulse, an apodised sine type time profile for a second pulse, a step type time profile for a third pulse, a Gaussian type time profile for a fourth pulse and a sinusoidal type time profile for a fifth pulse.

For example, a sinusoidal type time profile can be obtained using the formula $S(t)=A \sin(2\pi ft)$ in which $T \in [0 \ n \ T]$ T is the period of the signal, $T=1/f$;

N is the number of periods, and

A is the amplitude.

In the case of mechanical pulses with a sinusoidal type time profile, it is possible to vary the frequency, the number of periods and/or the amplitude. For example, the amplitude of each mechanical pulse may be between 10 μm and 10 mm, and preferably between 100 μm and 5 mm.

In summary, each mechanical pulse during this definition step 101 has a different characteristic from the other defined mechanical pulses. In other words, each defined mechanical pulse is different from the other mechanical pulses.

The multipulse elastography method 100 also comprises a step 102 to generate at least two mechanical pulses defined during the previous definition step 101, each of the at least two mechanical pulses generating a shear wave in a viscoelastic medium such that this wave propagates through this viscoelastic medium.

Figure 2:
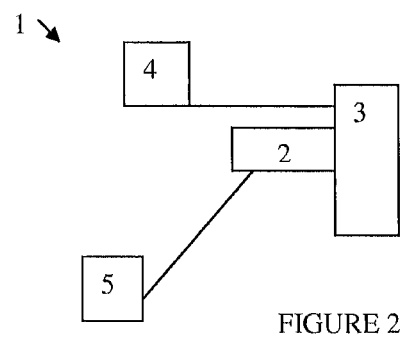
FIG. 2 diagrammatically illustrates an example multipulse elastography device according to the invention.

These mechanical pulses (indifferently called low frequency pulses) can be generated by a low frequency vibrator, or a loud speaker or any other type of vibration generator 2 (see FIG. 2) that is capable of generating a plurality of mechanical pulses, each mechanical pulse generating a low frequency shear wave in a viscoelastic medium such as human or animal biological tissue. The generation step 102 can be triggered automatically or manually. Manual triggering consists of an operator pressing a start button, while automatic triggering may be performed simply as soon as the viscoelastic medium applies pressure to the vibration generator.

Each of these mechanical pulses has a determined central frequency. The determined central frequency of these mechanical pulses is chosen between a minimum frequency that may for example be 10 Hz and a maximum frequency that may for example be 5000 Hz.

The multipulse elastography method 100 also comprises a step 103 to monitor propagation of at least two shear waves in the viscoelastic medium. This monitoring 103 is done by emission of ultrasonic signals in the viscoelastic medium and acquisition of ultrasonic signals reflected by the viscoelastic medium.

This monitoring step 103 is done using a single-element or multi-element ultrasonic transducer 3.

In one non-limitative example, each mechanical pulse has a different determined central frequency, in other words a different period. Consequently, each mechanical pulse has a different frequency band, this frequency band being formed from the central frequency of the mechanical pulse and the frequencies surrounding the central frequency.

Figure 3:
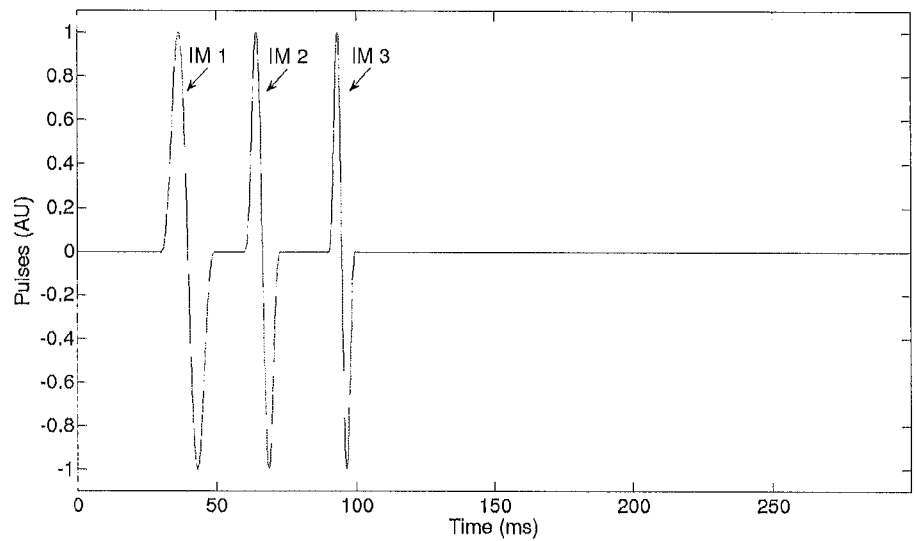
FIG. 3 illustrates three mechanical pulses each with a different central frequency, the three mechanical pulses having been generated using the method according to the invention.

As a non-limitative example illustrated in FIG. 3 during use of the method according to the invention on hepatic tissue:

a first shear wave is generated by a first mechanical pulse IM1 generated by the low frequency vibrator 2, the determined central frequency of this first mechanical pulse IM1 being 50 Hz;

a second shear wave is generated by the low frequency vibrator 2, this second shear wave is derived from a second mechanical pulse IM2 with a determined central frequency of 75 Hz;

a third shear wave is generated by the low frequency vibrator 2, this third shear wave is derived from a third mechanical pulse IM3 with a determined central frequency of 100 Hz.

In this example, the frequency bands of the mechanical pulses IM1, IM2 and IM3 at the source of the shear waves partially overlap. More precisely, the frequency band of the first mechanical pulse IM1 generating the first shear wave partially overlaps the frequency band of the second mechanical pulse IM2 generating the second shear wave, and the frequency band of the second mechanical pulse IM2 generating the second shear wave partially overlaps the frequency band of the third mechanical pulse IM3 generating the third shear wave. Consequently, the total frequency band is formed from the sum of the three frequency bands. This total frequency band can characterise the hepatic tissue more precisely than a smaller frequency band.

In this example, each mechanical pulse (mechanical pulse IM2 generating the second shear wave) succeeding a mechanical pulse (mechanical pulse IM1 generating the first shear wave) has a higher central frequency than the central frequency of the mechanical pulse preceding it (mechanical pulse IM1 generating the first shear wave).

It should be noted that this embodiment is not limitative and in one embodiment of the multipulse elastography method 100 according to the invention (not shown), each mechanical pulse (mechanical pulse IM2 generating the second shear wave) succeeding a mechanical pulse (mechanical pulse IM1 generating the first shear wave) has a lower central frequency than the central frequency of the mechanical pulse preceding it (mechanical pulse IM1 generating the first shear wave). This embodiment has the advantage that two succeeding shear waves do not mutually disturb each other. The shear wave attenuates more quickly as the frequency increases. Thus, if the central frequency of the first pulse IM1 generating the first shear wave is of the order of 100 Hz, in other words is higher than the central frequency (75 Hz) of the second pulse IM2 generating the second shear wave, then the first shear wave will be attenuated more quickly than the second shear wave thus reducing the risk of disturbance between the two shear waves.

Figure 4:
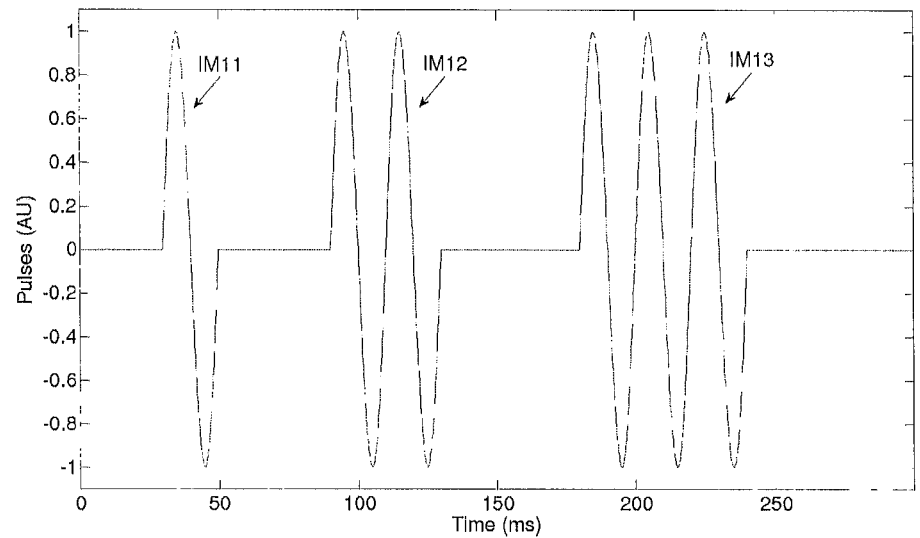
FIG. 4 illustrates mechanical pulses with different number of periods, the mechanical pulses having been generated using the method according to the invention.

In a different embodiment illustrated in FIG. 4, each defined mechanical pulse can have a different number of periods. For example, the first pulse IM11 has one period, the second pulse IM12 has two periods and the third pulse IM13 has three periods.

The multipulse elastography method 100 also comprises a step 104 to calculate at least one mechanical property of the viscoelastic medium by means of acquisitions of ultrasonic signals. This calculation step may be done when the step 103 is terminated.

In one non-limitative embodiment, the multipulse elastography method 100 also comprises a reiteration step 105 consisting of reiterating the generation step 102, the monitoring step 103 and the calculation step 104 at least once.

Figure 5:
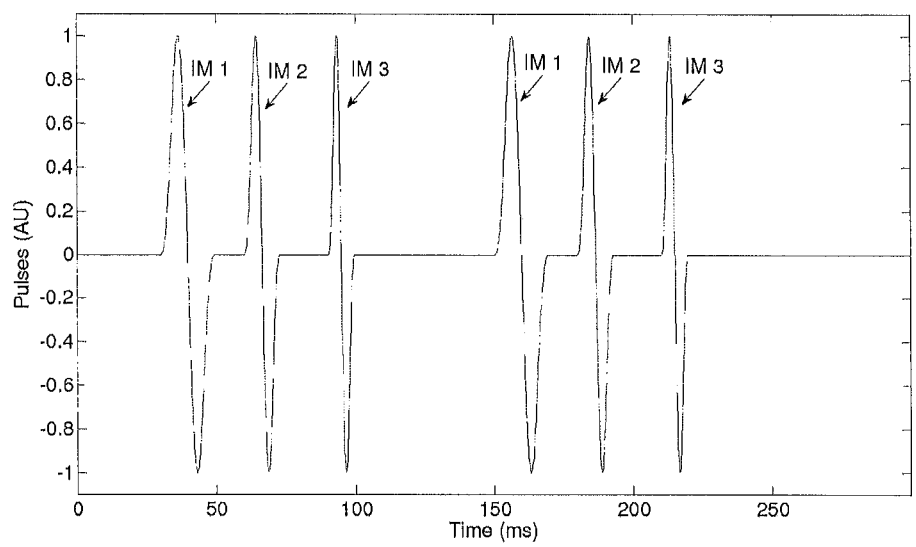
FIG. 5 illustrates a reiteration of the three mechanical pulses illustrated in FIG. 3.

The reiteration 105 of the generation step 102 is done at least once, as an example illustrated in FIG. 5. In this case, the three pulses and therefore the three shear waves are generated twice in the viscoelastic medium.

In a different embodiment, the reiteration 105 is done 20 times. When the characteristic that varies for each pulse generating the shear wave is the frequency, a limited number of times is sufficient to cover a sufficient frequency band to characterise a biological tissue while being limited in time to assure that the biological tissue does not move, for example due to internal biological movements such as breathing.

In one non-limitative embodiment, reiteration 105 of the generation, monitoring and calculation steps 102, 103 and 104 is triggered automatically. In other words, the operator using the multipulse elastography device 1 with the method 100 according to the invention does not need to trigger the reiteration step 105, since this step 105 is triggered automatically. In other words, the operator can predefine the number of reiterations 105 before starting the multipulse elastography method 100.

In a different embodiment, reiteration 105 of the generation, monitoring and calculation steps is triggered manually, in other words by the operator.

Therefore the disclosed invention provides a means of making a Vibration Controlled Transient Elastography (VCTE) type elastography acquisition composed of a series of pulses, for example made at different central frequencies between a minimum frequency and a maximum frequency. For example, each pulse can be used to study a frequency band around its central frequency. A complete characterisation of the medium on the range formed from the minimum frequency to the maximum frequency is obtained by juxtaposing the results obtained on each frequency band.

In particular, the method 100 according to the invention can be use to:
- explore a wide frequency range (complete characterisation of the medium),
- control the frequencies used,
- combine information received at several distinct frequencies,
- perform a fast and inexpensive, examination (compared with MRI),
- not move the probe fitted with the transducer between the different acquisitions (reduction in the variability of the measurement point),
- vary the minimum and maximum frequencies depending on the medium being studied,
- vary the number of periods
- vary the amplitude of shear waves,
- vary the pulse shape.

The invention also relates to a multipulse elastography device 1 comprising a vibration generator 2 capable of generating a plurality of mechanical pulses generating a plurality of shear waves and at least one ultrasonic transducer 3 capable of emitting and acquiring ultrasonic signals. The device 1 can be used to implement the steps in a multipulse elastography method 100 according to the invention, in other words the device 1 can be used to:
- define 101 the characteristics of at least two mechanical pulses through a human-machine interface HMI 5, each mechanical pulse generating a shear wave, at least one of the defined characteristics possibly being different for each mechanical pulse; these characteristics can be input by an operator using a keyboard,
- generate 102 the at least two defined mechanical pulses through the vibration generator 2, generating at least two shear waves in a viscoelastic medium,
- monitor 103 propagation in the viscoelastic medium through the ultrasonic transducer 3, of the at least two shear waves by ultrasonic signal emission and acquisition means, calculate 104 at least one mechanical property of the viscoelastic medium by ultrasonic signal acquisition means, using a computer 4.

It should be noted that throughout this description, during the step 101 to define the characteristics of at least two low frequency mechanical pulses, at least one characteristic of each of the mechanical pulses is different. Obviously, the invention is not limited to this embodiment and it may include a step 101 to define the characteristics of at least two low frequency mechanical pulses during which the characteristics of at least two low frequency mechanical pulses are identical. Some viscoelastic media have a very long relaxation time (in other words time to return to equilibrium). Therefore in this case the medium does not have time to return to equilibrium between the different pulses. Thus, information about the viscoelastic properties of the medium can be obtained by studying the propagation of shear waves generated consecutively by several similar pulses.

The invention claimed is:

1. A multipulse elastography method for quantitative measurement of at least one mechanical property of a viscoelastic medium having an ultrasonic signal after ultrasonic illumination, said method comprising:
    defining characteristics of at least two low-frequency mechanical pulses each having a central frequency comprised between 10 Hz and 5000 Hz, wherein at least the central frequency is different for each of the at least two low-frequency mechanical pulses, and wherein frequency bands of the at least two low-frequency mechanical pulses partially overlap;
    generating, in a viscoelastic medium, with a low-frequency vibration generator, said at least two low-frequency mechanical pulses for which the characteristics are defined;
    monitoring a propagation of at least two shear waves generated by said at least two low-frequency mechanical pulses using acquisition and emission of ultrasonic signals with at least one ultrasonic transducer that is distinct from said low-frequency vibration generator, in said viscoelastic medium, and
    calculating at least one mechanical property of said viscoelastic medium using said acquisitions of said ultrasonic signals.

2. The multipulse elastography method according to claim 1, further comprising reiterating the generating, the monitoring and the calculating.

3. The multipulse elastography method according to claim 2, wherein the reiteration is made between 1 and 1000 times.

4. The multipulse elastography method according to claim 1, wherein the at least one different characteristic is an amplitude.

5. The multipulse elastography method according to claim 4, wherein the amplitude of each of the at least two low-frequency mechanical pulses is between 10 μm and 10 mm.

6. The multipulse elastography method according to claim 1, wherein the at least one different characteristic is a time profile.

7. The multipulse elastography method according to claim 1, wherein the at least one different characteristic is a number of periods.

8. The multipulse elastography method according to claim 1, wherein the at least one different characteristic is a central frequency.

9. The multipulse elastography method according to claim 8, wherein the at least two low-frequency mechanical pulses succeed one another, and wherein the central frequency of a low-frequency mechanical pulse succeeding another low-frequency mechanical pulse is less than the central frequency of the other mechanical pulse.

10. The multipulse elastography method according to claim 9, wherein the central frequency of each of the at least two low-frequency mechanical pulses succeeding a low-frequency mechanical pulse is more than the central frequency of the preceding low-frequency mechanical pulse.

11. A multipulse elastography device, comprising:
    a low-frequency vibration generator configured to generate at least two low-frequency mechanical pulses each having a central frequency comprised between 10 Hz and 5000 Hz that generate a plurality of shear waves in a viscoelastic medium, wherein at least the central frequency is different for each of the at least two low-frequency mechanical pulses, and wherein frequency bands of the at least two low-frequency mechanical pulses partially overlap;
    at least one ultrasonic transducer configured to emit and acquire ultrasonic signals, the at least one ultrasonic transducer being distinct from said low-frequency vibration generator;
    a human-machine interface configured to define one or more characteristics of the at least two low-frequency mechanical pulses; and
    a computer configured to calculate at least one mechanical property of the viscoelastic medium using the acquisition of the ultrasonic signals,
    said device being configured to implement the multipulse elastography method according to claim 1.

12. The multipulse elastography method according to claim 3, wherein the reiteration is made between 1 and 20 times.

13. The multipulse elastography method according to claim 5, wherein the amplitude of each mechanical pulse is between 100 μm and 5 mm.

14. The multipulse elastography method according to claim 1, wherein the central frequency of each mechanical pulse is between 20 Hz and 1000 Hz.

15. A multipulse elastography method for quantitative measurement of at least one mechanical property of a viscoelastic medium having an ultrasonic signal after ultrasonic illumination, the method comprising:
    defining, via a human-machine interface, characteristics of at least two low-frequency mechanical pulses each having a central frequency comprised between 10 Hz and 5000 Hz, wherein at least the central frequency is different for each of the at least two low-frequency mechanical pulses, and wherein frequency bands of the at least two low-frequency mechanical pulses partially overlap;
    generating, in a viscoelastic medium, via a low-frequency vibration generator, the at least two low-frequency mechanical pulses in series for which the characteristics are defined;
    monitoring, via at least one ultrasonic transducer that is distinct from said low-frequency vibration generator, a propagation of at least two shear waves generated by the at least two low-frequency mechanical pulses using acquisition and emission of ultrasonic signals, in the viscoelastic medium, and
    calculating, via a computer, at least one mechanical property of the viscoelastic medium using the acquisition of the ultrasonic signals.

* * * * *